(12) United States Patent
Liu et al.

(10) Patent No.: US 12,121,753 B2
(45) Date of Patent: Oct. 22, 2024

(54) SYSTEMS AND METHODS FOR DETERMINING A RADIATION DOSE

(71) Applicant: SHANGHAI UNITED IMAGING HEALTHCARE CO., LTD., Shanghai (CN)

(72) Inventors: Yanfang Liu, Shanghai (CN); Huajie Han, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 17/823,500

(22) Filed: Aug. 30, 2022

(65) Prior Publication Data

US 2023/0067600 A1 Mar. 2, 2023

(51) Int. Cl.
*A61N 5/00* (2006.01)
*A61N 5/10* (2006.01)

(52) U.S. Cl.
CPC ......... *A61N 5/1071* (2013.01); *A61N 5/1075* (2013.01)

(58) Field of Classification Search
None
See application file for complete search history.

(56) References Cited

U.S. PATENT DOCUMENTS

| 6,636,622 | B2 | 10/2003 | Mackie et al. |
| 2010/0150309 | A1* | 6/2010 | Nord ............... A61N 5/1071 378/65 |
| 2015/0265224 | A1 | 9/2015 | Gerland |
| 2017/0296840 | A1 | 10/2017 | Bokrantz et al. |
| 2019/0076671 | A1 | 3/2019 | Willcut et al. |
| 2019/0192880 | A1 | 6/2019 | Hibbard |
| 2021/0187326 | A1 | 6/2021 | Han et al. |

FOREIGN PATENT DOCUMENTS

| CN | 104548372 A | 4/2015 |
| CN | 104645500 A | 5/2015 |
| CN | 107469239 A | 12/2017 |
| CN | 111001097 A | 4/2020 |
| CN | 111388879 A | 7/2020 |

(Continued)

OTHER PUBLICATIONS

Markus Wendling et al., A Simple Backprojection Algorithm for 3D in Vivo EPID Dosimetry of IMRT Treatments, Med. Phys., 36(7): 3310-3321, 2009.

*Primary Examiner* — Hoon K Song
(74) *Attorney, Agent, or Firm* — METIS IP LLC

(57) ABSTRACT

The embodiments of the present disclosure provide a system for determining a radiation dose. The system may include: obtaining data related to radiation source, a radiation auxiliary image of a target object at a target radiation time point, and an initial fluence map corresponding to the target radiation time point; determining a target fluence map corresponding to the target radiation time point by one or more iterations based on the radiation auxiliary image, the initial fluence map, and the data related to radiation source; obtaining a target scanning image of the target object; and determining the radiation dose received by the target object at the target radiation time point, based on the target fluence map, the target scanning image, and the data related to radiation source.

20 Claims, 9 Drawing Sheets

(56) References Cited

FOREIGN PATENT DOCUMENTS

| | | | |
|---|---|---|---|
| CN | 112151146 | A | 12/2020 |
| CN | 112382371 | A | 2/2021 |
| CN | 112546463 | A | 3/2021 |
| EP | 3391940 | A1 | 10/2018 |
| WO | 2014063748 | A1 | 5/2014 |
| WO | 2017054316 | A1 | 4/2017 |
| WO | 2017066248 | A1 | 4/2017 |

* cited by examiner

400

Obtaining data related to radiation source, a radiation auxiliary image of a target object at a target radiation time, and an initial fluence map corresponding to the target radiation time
402

Determining a target fluence map corresponding to the target radiation time by one or more iterations based on the radiation auxiliary image, the initial fluence map, and the data related to radiation source
404

Obtaining a target scanning image of the target object
406

Determining a radiation dose received by the target object at the target radiation time based on the target fluence map, the target scanning image, and the data related to radiation source
408

Obtaining a radiation auxiliary image of a target object at a target radiation time and an initial fluence map corresponding to the target radiation time
802

Determining a target fluence map corresponding to the target radiation time by one or more iterations at least based on the radiation auxiliary image, the initial fluence map, and data related to radiation source
804

```
┌─────────────────────────────────────────┐
│ Obtaining a radiation auxiliary image of a target │
│      object at a target radiation time      │
│                   902                     │
└─────────────────────────────────────────┘
                    ↓
┌─────────────────────────────────────────┐
│  Obtaining a plurality of scanning images of the  │
│   target object, the plurality of scanning images │
│  include a sequence of images corresponding to a  │
│         plurality of phases respectively          │
│                   904                     │
└─────────────────────────────────────────┘
                    ↓
┌─────────────────────────────────────────┐
│   Determining a target scanning image from the    │
│  plurality of scanning images based on the radiation │
│              auxiliary image              │
│                   906                     │
└─────────────────────────────────────────┘
                    ↓
┌─────────────────────────────────────────┐
│    Determining the radiation dose received by the │
│   target object at the target radiation time based on │
│     the target scanning image and the radiation   │
│              auxiliary image              │
│                   908                     │
└─────────────────────────────────────────┘
```

FIG. 9

SYSTEMS AND METHODS FOR DETERMINING A RADIATION DOSE

CROSS-REFERENCE TO RELATED APPLICATIONS

This application claims priority of Chinese Patent Application No. 2021110068301, filed on Aug. 30, 2021, the contents of which are hereby incorporated by reference.

TECHNICAL FIELD

The present disclosure relates to a medical radiation field, in particular, relates to systems and methods for determining a radiation dose.

BACKGROUND

A radiation dose distribution may be calculated during treatment, and a patient may be subjected to radiotherapy according to a determined radiation dose. The accuracy of the calculated radiation dose distribution may affect the evaluation of radiation effect, so the calculation of the radiation dose distribution is particularly important. Therefore, it is desirable to provide systems and methods for accurately determining a radiation dose that may be used to reconstruct an actual three-dimensional radiation dose received by the patient during the treatment.

SUMMARY

One aspect of the present disclosure may provide a system for determining a radiation dose in a radiotherapy. The system may include: at least one storage device storing a set of instructions; and at least one processor in communication with the storage device, wherein when executing the set of instructions, the at least one processor may be configured to cause the system to perform operations including: obtaining data related to radiation source, a radiation auxiliary image of a target object at a target radiation time point, and an initial fluence map corresponding to the target radiation time point; determining a target fluence map corresponding to the target radiation time point by one or more iterations based on the radiation auxiliary image, the initial fluence map, and the data related to radiation source; obtaining a target scanning image of the target object; and determining the radiation dose received by the target object at the target radiation time point, based on the target fluence map, the target scanning image, and the data related to radiation source.

Another aspect of the present disclosure may provide a system for determining a fluence map. The system may include: at least one storage device storing a set of instructions; and at least one processor in communication with the storage device, wherein when executing the set of instructions, the at least one processor may be configured to cause the system to perform operations including: obtaining a radiation auxiliary image of a target object at a target radiation time point and an initial fluence map corresponding to the target radiation time point; and determining a target fluence map corresponding to the target radiation time point by one or more iterations at least based on the radiation auxiliary image, the initial fluence map, and data related to radiation source.

Another aspect of the present disclosure may provide a system for determining a radiation dose. The system may include: at least one storage device storing a set of instructions; and at least one processor in communication with the storage device, wherein when executing the set of instructions, the at least one processor may be configured to cause the system to perform operations including: obtaining a radiation auxiliary image of a target object at a target radiation time point; obtaining a plurality of scanning images of the target object, the plurality of scanning images including a sequence of images corresponding to a plurality of phases respectively; determining a target scanning image from the plurality of scanning images based on the radiation auxiliary image; and determining the radiation dose received by the target object at the target radiation time point based on the target scanning image and the radiation auxiliary image.

BRIEF DESCRIPTION OF THE DRAWINGS

The present disclosure is further illustrated in terms of exemplary embodiments, and these exemplary embodiments are described in detail with reference to the drawings. These embodiments are not restrictive. In these embodiments, the same number indicates the same structure, wherein:

FIG. 4 is a flowchart illustrating an exemplary process for determining a radiation dose according to some embodiments of the present disclosure;

FIG. 8 is a flowchart illustrating an exemplary process for determining a fluence map according to some embodiments of the present disclosure;

FIG. 9 is a flowchart illustrating an exemplary process for determining a radiation dose according to some embodiments of the present disclosure.

DETAILED DESCRIPTION

Figure 1:
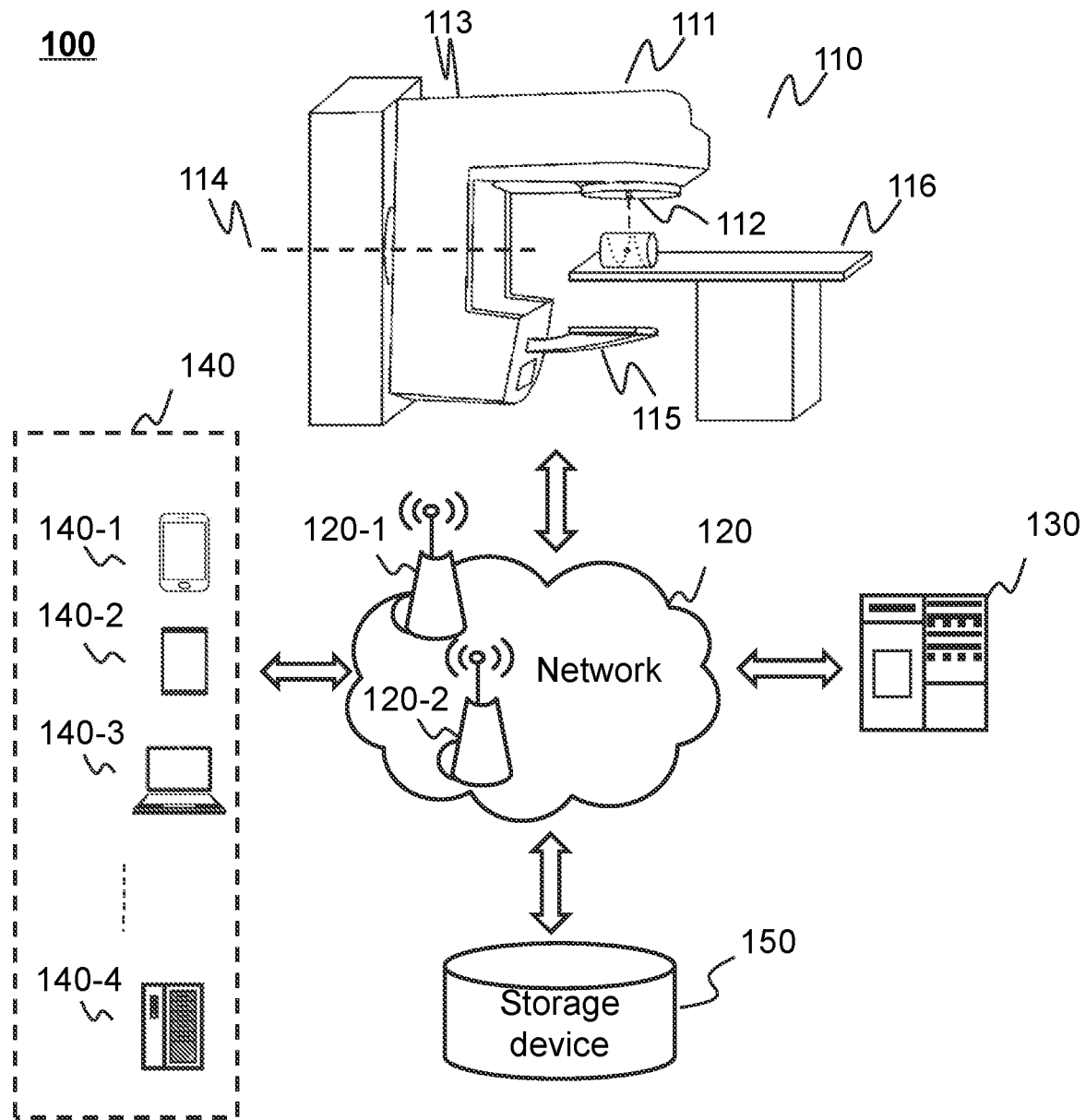
FIG. 1 is a schematic diagram illustrating an exemplary application scenario of a system for determining a radiation dose according to some embodiments of the present disclosure.

To more clearly illustrate the technical solutions related to the embodiments of the present disclosure, a brief introduction of the drawings referred to the description of the embodiments is provided below. Obviously, the accompanying drawing in the following description is merely some examples or embodiments of the present disclosure, for those skilled in the art, the present disclosure may further be applied in other similar situations according to the drawings without any creative effort. Unless obviously obtained from the context or the context illustrates otherwise, the same numeral in the drawings refers to the same structure or operation.

It will be understood that the term "system," "device," "unit," and/or "module" used herein are one method to distinguish different assemblies, elements, parts, sections or assemblies of different levels in ascending order. However, if other words may achieve the same purpose, the words may be replaced by other expressions.

As used in the disclosure and the appended claims, the singular forms "a," "an," and "the" include plural referents unless the content clearly dictates otherwise. Generally speaking, the terms "comprise" and "include" only imply that the clearly identified steps and elements are included, and these steps and elements may not constitute an exclusive list, and the method or device may further include other steps or elements.

The flowcharts used in the present disclosure illustrate operations that the system implements according to the embodiment of the present disclosure. It should be understood that a previous operation or a subsequent operation of the flowcharts may not be accurately implemented in order. Instead, a plurality of steps may be processed in reverse or simultaneously. Moreover, other operations may further be added to these procedures, or one or more steps may be removed from these procedures. The present disclosure describes a system for determining a radiation dose, the system may iteratively calculate an output flux of an accelerator based on a measured electronic portal imaging device (EPID) image and related parameters of a radioactive source, and may accurately reconstruct an actual three-dimensional (3D) dose received by a patient during treatment, and thus, a calculation model for determining the radiation dose may be greatly simplified and the calculation accuracy may be improved.

FIG. 1 is a schematic diagram illustrating an exemplary application scenario of a system for determining a radiation dose according to some embodiments of the present disclosure.

In some embodiments, a system 100 for determining a radiation dose may be applied to a medical system platform. For example, the system 100 may determine the radiation dose received by a target object (e.g., a patient) at a target radiation time point. As another example, the system 100 may determine the radiation dose received by the target object (e.g., a patient) through an obtained auxiliary image at the target radiation time point. As shown in FIG. 1, the system 100 may include a radiation device 110, a network 120, a processing device 130, a terminal 140, and a storage device 150. The various components in the system 100 may be connected with each other through the network 120. For example, the processing device 130 and the radiation device 110 may be connected or communicated through the network 120.

The radiation device 110 may transmit one or more radiation beams to the target object (e.g., a patient or a phantom). In some embodiments, the radiation device 110 may include a linear accelerator 111 (also may be referred to as linac). The linear accelerator 111 may generate and emit the radiation beam(s) (e.g., an X-ray beam) from a treatment head 112. The radiation beam(s) may pass through one or more collimators with a specific shape (e.g., a multi-leaf collimator) and be transmitted to the target object. In some embodiments, the radiation beam(s) may include electrons, photons, or any other types of radiation. In some embodiments, energy of the radiation beam(s) may be in a megavolt level (i.e., >1 MeV), and the radiation beam(s) may also be referred to as megavolt radiation beam(s). The treatment head 112 may be coupled to a gantry 113. The gantry 113 may rotate, for example, clockwise or counterclockwise around a gantry rotation axis 114. The treatment head 112 may rotate with the gantry 113 together. In some embodiments, the radiation device 110 may include an imaging assembly 115. The imaging assembly 115 may receive the radiation beam(s) passing through the target object and acquire projection image(s) of the patient or the phantom before, during, and/or after the radiation or correction process. The imaging assembly 115 may include an analog detector, a digital detector, or any combination thereof. The imaging assembly 115 may be attached to the gantry 113 in any manner, and/or include a retractable housing. Therefore, when the gantry 113 rotates, the treatment head 112 and the imaging assembly 115 may rotate synchronously. In some embodiments, the imaging assembly 115 may include an EPID. In some embodiments, the radiation device 110 may also include a bed 116. The bed 116 may support the patient during the radiation or imaging, and/or support the phantom during the correction process of the radiation device 110. The bed 116 may be adjusted according to different application scenarios.

The network 120 may include any suitable network capable of facilitating the exchange of information and/or data of the system 100. The information and/or data may include one or more radiation auxiliary images transmitted from the radiation device 110 to the processing device 130. For example, the processing device 130 may obtain the radiation auxiliary image (e.g., an EPID image) determined by the imaging assembly 115 from the radiation device 110 via the network 120. As another example, the processing device may obtain user (e.g., a doctor) instruction from the terminal 140 via the network 120. In some embodiments, the network 120 may be any type of wired or wireless network. For example, the network 120 may include cable network, wired network, optical fiber network, telecommunication network, internal network, Internet, area network (LAN), wide area network (WAN), wireless area network (WLAN), metropolitan area network (man), public switched telephone network (PSTN), Bluetooth network, ZigBee network, near field communication (NFC) network, ultra-wideband (UWB) network, mobile communication (1g, 2G, 3G, 4G, 5g) network, narrowband Internet of things (NB IoT), infrared communication network, or any combination thereof. In some embodiments, the network 120 may include one or more network access points. For example, the network 120 may include wired or wireless network access points, such as base stations and/or internet switching points 120-1, 120-2, . . . , through these access points, one or more components of the system 100 may be connected with the network 120 to exchange the data and/or information.

The terminal 140 may communicate and/or be connected with the radiation device 110, the processing device 130, and/or the storage device 150. For example, the terminal 140 may determine a dose determination result during the radiotherapy from the processing device 130. As another example, the terminal 140 may obtain an image (e.g., a radiation auxiliary image) acquired by the radiation device 110., and transmit the image to the processing device 130 for processing. In some embodiments, the terminal 140 may include a mobile device 140-1, a tablet computer 140-2, a laptop computer 140-3, a desktop computer 140-4, or any combination thereof. For example, the mobile device 140-1 may include a mobile phone, a personal digital assistant (PDA), a game device, a navigation device, or any combination thereof. In some embodiments, the terminal 140 may include an input device, an output device, or the like. The input device may include alphanumeric and other keys. The input device may choose a keyboard input, a touch screen (e.g., with tactile or tactile feedback) input, a voice input, an eye-tracking input, a brain monitoring system input, or any other similar input mechanism. Input information received by the input device may be transmitted to the processing device 130 via a bus for further processing. The other types of input devices may include a cursor control device, such as a mouse, a trackball, a cursor direction key, or the like. The output device may include a display, a speaker, a printer, or any combination thereof. In some embodiments, the terminal 140 may be part of the processing device 130. In some embodiments, the terminal 140 and the processing device 130 may be integrated as a control device of the radiation device 110, such as an operation console. In some embodiments, the terminal 140 may be omitted.

The storage device 150 may store data, instructions, and/or any other information. In some embodiments, the storage device 150 may store information for behaviors of a user to control the radiation device 110. In some embodiments, the storage device 150 may store data obtained from the radiation device 110, the terminal 140, and/or the processing device 130. In some embodiments, the storage device 150 may store data and/or instructions used by the processing device 130 to perform or use to accomplish the example methods described in the present disclosure. In some embodiments, the storage device 150 may include a mass storage, a removable memory, a volatile read-write memory, a read-only memory (ROM), or any combination thereof. The exemplary mass storage may include a magnetic disk, an optical disk, a solid state disk, or the like. The exemplary removable storage may include a flash drive, a floppy disk, an optical disk, a memory card, a compact disk, a magnetic tape, or the like. The exemplary volatile read-write memory may include a random access memory (RAM). The exemplary RAM may include a Dynamic Random Access Memory (DRAM), a Double Data Rate Synchronous Dynamic Random Access Memory (DDRS-DRAM), a Static Random Access Memory (SRAM), a Thyristor Random Access Memory (T-RAM), and a Zero Capacitance Random Access Memory (Z-RAM), etc. The exemplary read-only memory may include a masked read-only memory (MROM), programmable read-only memory (PROM), an erasable programmable read-only memory (EPROM), an electrically erasable programmable read-only memory (EEPROM), an optical disk read-only memory (CD-ROM), a digital multifunctional disk read-only memory, or the like. In some embodiments, the storage device 150 may be implemented on a cloud platform.

In some embodiments, the storage device 150 may be connected with the network 120 to communicate with at least one other component (e.g., the processing device 130, the terminal 140) in the system 100. At least one component of the system 100 may access data or instructions stored in the storage device 150 via the network 120. In some embodiments, the storage device 150 may be part of the processing device 130.

In some embodiments, the system 100 may also include one or more power supplies (not shown in FIG. 1) connected with one or more components of the system 100 (e.g., the processing device 130, the radiation device 110, the terminal 140, the storage device 150, etc.). It should be noted that the above description is provided for illustrative purposes only and is not intended to limit the scope of the present disclosure. For those skilled in the art, many changes and modifications can be made under the guidance of the content of the present disclosure. The features, structures, methods, and other features of the exemplary embodiments described herein may be combined in various ways to obtain additional and/or alternative exemplary embodiments. For example, the storage device 150 may be a data storage device including a cloud computing platform, such as a public cloud, a private cloud, a community, a hybrid cloud, and the like. However, these changes and modifications may not deviate from the scope of the present disclosure.

Figure 2:
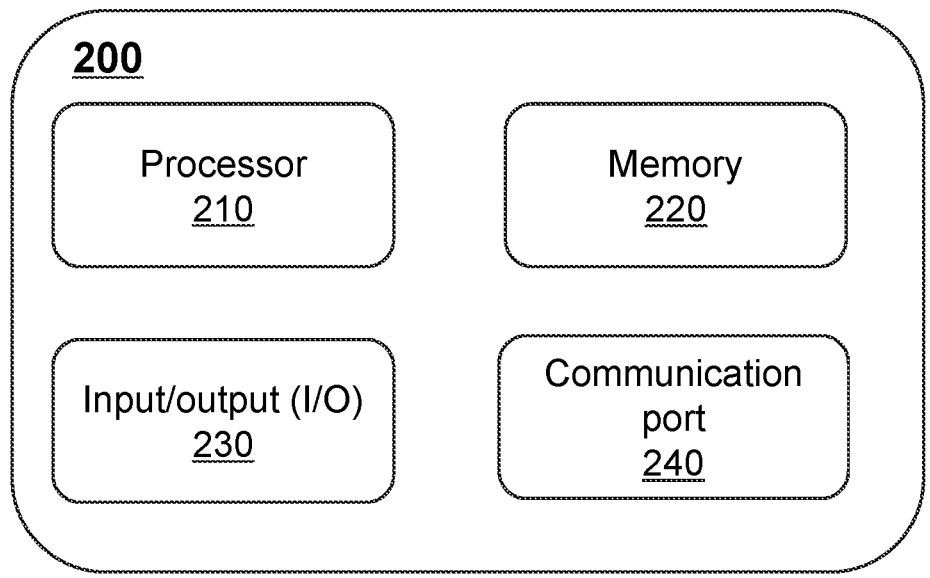
FIG. 2 is a schematic diagram illustrating an exemplary hardware and/or software components of a computing device according to some embodiments of the present disclosure.

FIG. 2 is a schematic diagram illustrating an exemplary hardware and/or software components of a computing device according to some embodiments of the present disclosure.

A computing device 200 may include a processor 210, a memory 220, an input/output (I/O) 230, and a communication port 240.

The processor 210 may execute computer instructions (e.g., program code) and perform functions of the processing device 130 according to the method(s) described herein. The computer instructions may include, for example, routines, programs, objects, components, data structures, procedures, modules, and functions, which perform particular functions described herein. For example, the processor 210 may process data of the radiation device 110, the terminal 140, the storage device 150, and/or any other component in the system 100. In some embodiments, the processor 210 may include at least one hardware processor, such as a microcontroller, microprocessor, reduced instruction set computer (RISC), application specific integrated circuit (ASIC), application specific instruction set processor (ASIP), central processing unit (CPU), graphics processing unit (GPU), physical processing unit (PPU), microcontroller unit, digital signal processor (DSP), field programmable gate array (FPGA), high-order RISC Machine (ARM), programmable logic device (PLD), any circuit or processor or similar capable of performing at least one function, or any combination thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operations A and B, it should be understood that operation A and operation B may also be performed by two or more different processors jointly or separately in the computing device 200 (e.g., a first processor executes operation A and a second processor executes operation B, or the first and second processors jointly execute operations A and B).

The memory 220 may store data/information obtained from the radiation device 110, the terminal 140, the storage device 150, and/or any other component in the system 100. In some embodiments, the memory 220 may include a mass storage, a removable storage, a volatile read-write memory, a read-only memory (ROM), or any combination thereof. For example, the mass storage may include a magnetic disk, an optical disk, a solid-state hard disk, or the like. The removable memory may include a flash drive, a floppy disk, an optical disk, a memory card, a compressed disk, a magnetic tape, etc. The volatile read and write memory may include a random access memory (RAM). The RAM may include a dynamic RAM (DRAM), a double rate synchronous dynamic RAM (DDRSDRAM), a static RAM (SRAM), a thyristor RAM (t-ram), a zero capacitance (Z-RAM), etc. The exemplary read-only memory may include a masked read-only memory (MROM), a programmable read-only memory (PROM), an erasable programmable read-only memory (EPROM), an electrically erasable programmable read-only memory (EEPROM), an optical disk read-only memory (CD-ROM), a digital multifunctional disk read-only memory, or the like. In some embodiments, the memory 220 may store at least one program and/or instruction for executing the exemplary manner described in the present disclosure.

The input/output (I/O) 230 may be used to input and/or output signal, data, information, etc. In some embodiments, the input/output (I/O) 230 may enable the user to interact with processing device 130. In some embodiments, the input/output (I/O) 230 may include an input device and an output device. An exemplary input device may include a keyboard, a mouse, a touch screen, a microphone, or any combination thereof. The exemplary output device may include a display device, a speaker, a printer, a projector, or any combination thereof. An exemplary display device may include a liquid crystal display (LCD), a light emitting diode (LED)-based display, a flat panel display, a curved surface display, a television device, a cathode ray tube, or any combination thereof.

The communication port 240 may be connected with a network (e.g., the network 120) to facilitate data communication. The communication port 240 may establish a connection between the processing device 130 and the radiation device 110, the terminal 140, and/or the storage device 150. The connection may include a wired connection and a wireless connection. The wired connection may include, for example, cable, optical cable, telephone line, or any combination thereof. The wireless connection may include, for example, Bluetooth link, Wi-Fi™ link, WiMax™ link, WLAN link, ZigBee link, mobile network link (e.g., 3G, 4G, 5g, etc.), or any combination thereof. In some embodiments, the communication port 240 may be and/or include a standardized communication port, such as RS232, RS485, etc. In some embodiments, the communication port 240 may be a specially designed communication port. For example, the communication port 240 may be designed according to a digital imaging and medical communication (DICOM) protocol.

Figure 3:
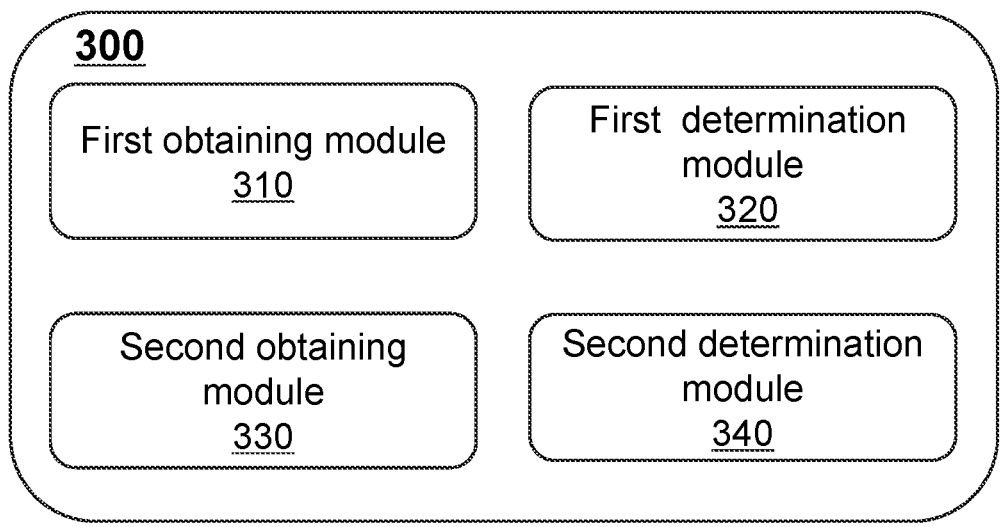
FIG. 3 is a block diagram illustrating an exemplary system for determining a radiation dose according to some embodiments of the present disclosure.

FIG. 3 is a block diagram illustrating an exemplary system for determining a radiation dose according to some embodiments of the present disclosure.

As shown in FIG. 3, the processing device 130 may include a first obtaining module 310, a first determination module 320, a second obtaining module 330, and a second determination module 340.

The first obtaining module 310 may be used to obtain data related to radiation source, a radiation auxiliary image of the target object at the target radiation time point, and an initial fluence map corresponding to the target radiation time point. The data related to radiation source may be used to describe parameters of devices and/or assemblies related to ray delivery. The devices and/or assemblies may include a radioactive source, an accelerator, a collimator, or the like. The exemplary parameters may include a radiation beam energy, a radiation beam spot size, collimator physical parameters (such as a blade length, a blade thickness, or a range of motion of a multi-leaf collimator), etc. The radiation auxiliary image may include a medical image obtained by the imaging assembly of the radiation device based on data generated by received ray(s) passing through the target object during the radiation. The radiation auxiliary image may include an EPID image. In some embodiments, the initial fluence map corresponding to the target radiation time point may be a preset image. For example, the initial fluence map may be any medical image. As another example, the initial fluence map may be an image obtained by processing the data received by the imaging assembly after radiation beam(s) emitted by the radiation device passes through the phantom.

In some embodiments, the data related to radiation source may include a source model of the radioactive source.

The first determination module 320 may be used to determine a target fluence map corresponding to the target radiation time point by one or more iterations based on the radiation auxiliary image, the initial fluence map, and the data related to radiation source. The target fluence map may reflect relevant state information of the radioactive source at the target radiation time point. The first determination module 320 may determine a final target fluence map by repeatedly simulating, for example, a physical motion process of chief ray particles. The first determination module 320 may repeatedly determine and update the fluence map in one or more iterations. A current iteration of the one or more iterations may include a simulation and a process of updating the fluence map. In some embodiments, the radiation auxiliary image may be a corrected image. For example, the first determination 320 may correct the radiation auxiliary image to obtain a corrected radiation auxiliary image, and determine a target fluence map corresponding to the target radiation time point by the one or more iterations based on the corrected radiation auxiliary image, the initial fluence map, and the data related to radiation source. In some embodiments, the correction may include bad point correction, dark current correction, gain correction, geometric correction, or any combination thereof.

In some embodiments, in the current iteration of the one or more iterations, the first determination module 320 may obtain object information of the target object, and determine a prediction image of radiation in the current iteration based on the data related to radiation source, a current fluence map corresponding to the current iteration, and the object information of the target object. The object information of the target object may include scanning image information of the target object (e.g., a positioning image of the target object, a plan image of the target object). The exemplary scanning image information may include Computed Radiography (CR) image information, Digital Radiography (DR) image information, Computed Tomography (CT) image information, Magnetic Resonance Imaging (MRI) image information, Positron Emission Computed Tomography (PET) image information, or any combination thereof. In some embodiments, the object information may be acquired in advance before the target radiation time point. In some embodiments, the first determination module 320 may determine the prediction image of radiation in the current iteration based on the data related to radiation source, the current fluence map corresponding to the current iteration, and the object information of the target object using a Monte Carlo Method.

In some embodiments, the first determination module 320 may determine whether the radiation auxiliary image and the prediction image of radiation in the current iteration satisfy a first judgment condition. The first judgment condition may include a prediction image of radiation in the current iteration being convergent to the radiation auxiliary image. The convergence may mean that a difference between the prediction image of radiation and the radiation auxiliary image in the current iteration is less than a preset threshold. The difference may be related to a difference between pixel values of the corresponding pixels in the two images. In response to the radiation auxiliary image and the prediction image of radiation in the current iteration satisfying the first judgment condition, the first determination module 320 may designate the current fluence map corresponding to the current iteration as the target fluence map. In response to the radiation auxiliary image and the prediction image of radiation in the current iteration do not satisfy the first judgment condition, the first determination module 320 may update the current fluence map corresponding to the current iteration, and designate the updated current fluence map corresponding to the current iteration as a current fluence map corresponding to a next iteration. The first determination module 320 may determine a first difference between the radiation auxiliary image and the prediction image of radiation in the current iteration. The first difference may be a first difference matrix between a first matrix representing the radiation auxiliary image and a second matrix representing the prediction image of radiation in the current iteration. The first determination module 320 may update a current fluence map corresponding to the current iteration based on the first difference.

In some embodiments, in the current iteration of the one or more iterations, the first determination module 320 may obtain the object information of the target object, and determine a prediction image of main radiation beam and a scattering ratio in the current iteration based on the data related to radiation source, the current fluence map corresponding to the current iteration, and the object information of the target object. The prediction image of main radiation beam may be an image formed by chief ray particles after removing scattering particles from the radiation beam. The scattering ratio may be a ratio between the amount of the scattering particles and the amount of the chief ray particles. In some embodiments, the first determination module 320 may determine a prediction image of main radiation beam and a scattering ratio in the current iteration based on the data related to radiation source, the current fluence map corresponding to the current iteration, and the object information of the target object using the Monte Carlo Method.

In some embodiments, the first determination module 320 may determine a descattering reference image in the current iteration based on the scattering ratio and the radiation auxiliary image and determine whether the descattering reference image and the prediction image of main radiation beam in the current iteration satisfy a second judgment condition. The descattering reference image may be determined based on the chief ray particles in an actual dose captured by a detection assembly of the radiation device. The second judgment condition may include the prediction image of main radiation beam in the current iteration being convergent to the descattering reference image in the current iteration. The convergence may mean that a difference between the prediction image of main radiation beam in the current iteration and the descattering reference image in the current iteration is less than a preset threshold. The difference may be a difference between the pixel values of the corresponding pixels in the two images. In response to the descattering reference image and the prediction image of main radiation beam in the current iteration satisfying the second judgment condition, the first determination module may designate the current fluence map corresponding to the current iteration as the target fluence map. In response to the descattering reference image and the prediction image of main radiation beam in the current iteration not satisfying the second judgment condition, the first determination module 320 may update the current fluence map corresponding to the current iteration and designate the updated current fluence map corresponding to the current iteration as a current fluence map corresponding to a next iteration. In some embodiments, the first determination module may determine a second difference between the descattering reference image and the prediction image of main radiation beam in the current iteration. The second difference may be a second difference matrix between a third matrix representing the descattering reference image in the current iteration and a fourth matrix representing the prediction image of main radiation beam in the current iteration. The first determination module 320 may update the current fluence map corresponding to the current iteration based on the second difference.

The second obtaining module 330 may be used to obtain a target scanning image of the target object. In some embodiments, the second obtaining module 330 may obtain a plurality of scanning images of the target object before the target radiation time point and determine a plurality of prediction phase images of the target object at the target radiation time point corresponding to the plurality of phases respectively. The plurality of scanning images may reflect different motion states of the target object in one or more autonomous motion cycles. The plurality of scanning images may be pre-scanned and determined before the target radiation time point. In some embodiments, the plurality of scanning images may include one or more four-dimensional computed tomography (4D-CT) images obtained based on an T imaging device or one or more online 4D-CT images. In some embodiments, a prediction phase image may refer to a prediction image reflecting a state of the target object at the target radiation time point. In order to determine the plurality of prediction phase images corresponding to the plurality of phases respectively, the second obtaining module 330 may obtain treatment planning information and determine planning delivery information at the target radiation time point based on the treatment planning information. The planning delivery information may include a radiation beam intensity, a radiation beam conformal shape, a radiation dose, or the like. For each phase of the plurality of phases, the second obtaining module 330 may obtain relevant information of the phase. The relevant information of the phase may include state information or phase information of the target object in the phase. For example, the relevant information of the phase may include stages of physiological movement (e.g., systolic phases of cardiac movement, diastolic phases of cardiac movement, etc.) of the target object (e.g., a patient, organ, or tissue of a patient), postures (such as lying down, lying on the side, etc.), a state, or a body shape of the target object, etc. The second obtaining module 330 may determine the prediction phase image corresponding to the phase based on the planning delivery information and the relevant information of the phase. For example, the second obtaining module 330 may obtain the prediction phase image using simulation.

In some embodiments, the second obtaining module 330 may determine, from the plurality of prediction phase images, a matched image that matches the radiation auxiliary image. The matched image may refer to a prediction phase image similar to the radiation auxiliary image corresponding to the target radiation time point. For example, the state of the target object displayed in the matched image may be the closest to the state of the target object displayed in the radiation auxiliary image. In some embodiments, the second obtaining module 330 may determine the matched image that matches the radiation auxiliary image using a feature matching algorithm. For example, the second obtaining module 330 may compare a feature distribution (e.g., a grayscale distribution) of each of the plurality of prediction phase images with a feature distribution (e.g., a grayscale distribution) of the radiation auxiliary image and choose the prediction phase image whose feature distribution is closest to the feature distribution of the radiation auxiliary image as the matched image. In some embodiments, the second obtaining module 330 may determine first position information of a target tissue included in the radiation auxiliary image and second position information of the target tissue included in each image of the plurality of the prediction phase images. The target tissue may refer to an identifiable tissue in the target object, such as tumor area or organ. The second obtaining module 330 may determine the matched image of the radiation auxiliary image based on the first position information and the second position information. For example, the second obtaining module 330 may compare the first position information and the second position information corresponding to each prediction phase image. If the first position information matches the second position information corresponding to a prediction phase image, the second obtaining module 330 may designate the prediction phase image as the matched image.

In some embodiments, the second obtaining module may determine a third difference of each prediction phase image in the plurality of prediction phase images and the radiation auxiliary image. The third difference may refer to a difference between a matrix representing the radiation auxiliary image and a matrix representing the prediction phase image. The second obtaining module 330 may determine a minimum value in the plurality of third differences, and designate the prediction phase image corresponding to the minimum value as the matched image.

In some embodiments, the second obtaining module 330 may determine a target phase corresponding to the matched image and designate a scanning image corresponding to the target phase as the target scanning image.

The second determination module 340 may be used to determine the radiation dose received by the target object at the target radiation time point based on the target fluence map, the target scanning image, and the data related to radiation source. The second determination module 340 may determine the radiation dose received by the target object at the target radiation time point using the Monte Carlo Method. In some embodiments, the Monte Carlo method may be used to simulate various physical processes of ray particles in the target object (e.g., scattering, attenuation, etc.). For example, the second determination module 340 may simulate a transport process of the ray particles using the Monte Carlo method, for example, under a parameter condition of devices and/or assemblies used for ray delivery as reflected by the data related to radiation source and a condition of the radioactive source reflected by the target fluence map, after rays pass through an inner region of the target object reflected by the target scanning image, a final dose distribution may be obtained. Based on the dose distribution, the second determination module 340 may determine the radiation dose received by the target object at the target radiation time point.

In some embodiments, the processing device 130 may further include a third determination module (not shown). The third determination module may obtain the radiation dose received by the target object during radiation at a plurality of radiation times and determine a total radiation dose received by the target object during the radiation based on the radiation dose received at the plurality of radiation times.

More descriptions of the above modules may be found elsewhere in the present disclosure (e.g., FIGS. 4-7 and descriptions thereof).

It should be understood that the system and its modules shown in FIG. 3 may be implemented in various ways. For example, in some embodiments, the system and its modules may be implemented in hardware, software, or a combination thereof. The hardware part may be implemented by logic circuits; the software part may be stored in memory and executed by a suitable instruction execution system, such as a microprocessor or specially designed hardware. Those skilled in the art may understand that the above methods and systems can be implemented using computer executable instructions and/or contained in processor control code, such as providing such code on a carrier medium such as magnetic disk, CD or DVD-ROM, a programmable memory such as read only memory (Firmware), or a data carrier such as an optical or electronic signal carrier. The system and its modules of the present disclosure may be implemented not only by hardware circuits such as Very Large Scale Integration (VLSI) or gate arrays, semiconductors such as logic chips and transistors, or programmable hardware devices such as field programmable gate arrays and programmable logic devices but also by software executed by various types of processors, it may also be realized by the combination of the above hardware circuits and software (e.g., firmware).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the first obtaining module 310 and the second obtaining module 330 shown in FIG. 3 may be different modules in a system, or one module may realize the functions of the above two or more modules. As another example, each module may share one storage module, and each module can also have its own storage module. Such deformations are within the scope of protection of the present disclosure.

FIG. 4 is a flowchart illustrating an exemplary process for determining a radiation dose according to some embodiments of the present disclosure. In some embodiments, process 400 may be executed by the system 100. For example, the process 400 may be implemented as a set of instructions (e.g., an application) stored in a storage device (e.g., the storage device 150, and/or the memory 220). In some embodiments, the processing device 130 (e.g., the processor 210 of the computing device 200, and/or one or more modules illustrated in FIG. 3) may execute the set of instructions and may accordingly be directed to perform the process 400. The operations of the illustrated process presented below are intended to be illustrative. In some embodiments, the process 400 may be accomplished with one or more additional operations not described and/or without one or more of the operations discussed. Additionally, the order of the operations of process 400 illustrated in FIG. 4 and described below is not intended to be limiting.

In 402, the data related to radiation source, the radiation auxiliary image of the target object at the target radiation time point, and the initial fluence map corresponding to the target radiation time point may be obtained. The operation may be executed by the first obtaining module 310.

In some embodiments, the data related to radiation source may be used to describe parameters of devices and/or assemblies related to ray delivery. The devices and/or assemblies may include a radioactive source, an accelerator, a collimator, or the like. Exemplary parameters may include a radiation beam energy, a radiation beam spot size, collimator physical parameters (e.g., a blade length, a blade thickness, a range of motion, or the like, of a multi-leaf collimator), etc. In some embodiments, the data related to radiation source may be obtained through calibration. For example, the radiation device may delivery radiation rays to a phantom (e.g., a water phantom), phantom data (e.g., a phantom thickness) and radiation auxiliary image data (e.g., EPID image data) may be acquired, and the data related to radiation source may be determined based on the acquired data.

It should be noted that before the target object (e.g., a cancer patient, a cancerous organ or tissue of the cancer patient, etc.) is treated by radiation rays, a radiation treatment plan may be determined. The treatment plan may indicate operations of the radiation device (e.g., the radiation device 110) throughout the radiation period. For example, the treatment plan may specify a plurality of nodes (also be referred to as control nodes), and each control node may correspond to a time point. The treatment plan may indicate a rotation angle of the gantry 113, moving positions of leaves of the multi-leaf collimator and/or the tungsten gate, a dose of rays emitted by the linear accelerator 111, or the like, at each time point. The radiation rays may be emitted at the control nodes (e.g., in a static intensity modulated radiation) or may be emitted continuously between two control nodes (e.g., in a dynamic intensity modulated radiation). Therefore, the target radiation time point may be a time point corresponding to the control node, or a time point between two control nodes. In some embodiments, at the target radiation time point, the radiation device (e.g., the radiation device 110) may begin or stop to emit radiation rays.

In addition, the radiation rays may be incompletely absorbed after passing through the target object, and a portion of the radiation rays may be received by an imaging assembly (e.g., the imaging assembly 115) after being attenuated. The imaging assembly 115 may be used to image the target object after the target object receives the radiation rays and an image may be generated. The obtained image may be used to assist the radiation. For example, the position of the target object may be confirmed (or verified), or the actual dose received by the target object may be determined. Therefore, after the radiation rays delivered by the radioactive source (e.g., the linear accelerator 111) pass through the target object, an image may be generated the imaging assembly (e.g., the imaging assembly 115), and the image may be referred to as the radiation auxiliary image.

In some embodiments, the radiation auxiliary image may include an EPID image. For example, the imaging assembly 115 may be an EPID. A detector in the EPID may detect the radiation rays passing through the target object and the detected radiation rays may be converted into electrical signals or digital signals (which may also be referred to as projection data). In some embodiments, the EPID image may be obtained by reconstruction based on the electrical signals or digital signals.

The fluence map may be referred to as an image that reflects a state of ray emission. For example, the fluence map may reflect the position of the collimator (e.g., the positions of the plurality of leaves of a multi-leaf collimator), the radiation beam intensity, or the like. In some embodiments, the initial fluence map corresponding to the target radiation time point may be a preset image. For example, the initial fluence map may be a preset CT image, or a CT image converted from another image with another modality (e.g., a PET image, an MRI image, etc.). As another example, the initial fluence map may be an image reconstructed based on data received by the imaging assembly after the radiation device emits radiation rays to the phantom. The initial fluence map may be pre-stored in the storage device (e.g., the storage device 150). The first obtaining module 310 may communicate with the storage device 150 to obtain the initial fluence map. In some embodiments, the initial fluence map corresponding to the target radiation time point may be obtained based on the radiation auxiliary image corresponding to the target radiation time point. For example, the first obtaining module 310 may obtain the initial fluence map by normalizing the radiation auxiliary image corresponding to the target radiation time point.

In 404, a target fluence map corresponding to the target radiation time point may be determined by one or more iterations based on the radiation auxiliary image, the initial fluence map, and the data related to radiation source. The operation 404 may be performed by the first determination module 320.

In some embodiments, the target fluence map may be an image that reflects state information of the radioactive source at the target radiation time point. It may be understood that the radiation rays may be captured by the detection assembly (e.g., the imaging assembly 115 of the radiation device 110) of the radiation device. The imaging assembly 115 may generate a corresponding image (e.g., the radiation device) based on the captured information. The radiation auxiliary image may reflect a ray dose (also be referred to as a radiation dose) received by the imaging assembly 115. According to the data related to radiation source that reflects the parameter of the devices and/or assemblies relating to the ray delivery and the initial fluence map that reflects the state information of the radioactive source, and/or other data (e.g., such as attenuation and/or absorption information of the radiation rays that pass through the target object), the first determining module 320 may determine the state information of the radioactive source at the target radiation time point. For example, the first determination module 320 may simulate a final target fluence map according to a physical motion process of the ray particles. The first determination module 320 may determine and update the fluence map repeatedly by the one or more iterations. Each iteration may be a simulation and updating process of the fluence map. After the iteration is terminated, the final fluence map may be determined as the target fluence map.

In some embodiments, the first determination module 320 may calibrate the radiation auxiliary image to obtain a calibrated radiation auxiliary image, and the target fluence map corresponding to the target radiation time point may be determined by the one or more iterations based on the calibrated radiation auxiliary image, the initial fluence map, and the data related to radiation source. In some embodiments, the calibration may include bad pixel calibration, dark current calibration, gain calibration, geometry calibration, etc., or any combination thereof.

In 406, a target scanning image of the target object may be obtained. The operation 406 may be performed by the second determination module 330.

In some embodiments, the target scanning image may correspond to the target radiation time point. The target scanning image may reflect the state of the target object at the target radiation time point. In some embodiments, during radiotherapy, the target object (e.g., a patient) may be moving autonomously (e.g., through physiological movements such as heartbeat, breathing, etc.). The state of the target object at the target radiation time point (e.g., a motion state of the chest of the patient due to breathing) may be used to guide the radiotherapy. For example, different motion states of the chest of the patient may affect dose distribution in the patient's body, and the position of the target region may change. Therefore, the target scanning image may be used in subsequent operations of the process 400 (e.g., be used to determine the radiation dose).

In some embodiments, the state of the target object at the target radiation time point may be considered as roughly the same as the state before the radiation time, therefore, the target scanning image of the target object corresponding to the target radiation time point may be considered to be similar to the scanning image of the target object before the radiation time (i.e., the scanning image of the target object before the radiation time may be used as the target scanning image of the target object corresponding to the target radiation time point). In some embodiments, the target scanning image may be an image obtained by scanning the target object before the target radiation time point. For example, before the radiotherapy, the target object may be scanned and imaged. The target scanning image may be determined from a plurality of obtained scanning images. In some embodiments, the target scanning image may be determined based on an X-ray imaging device (e.g., a computed radiograph (CR), a digital radiograph (DR), a computed tomography (CT), a mobile X-ray device (e.g., a mobile C-arm), a digital subtraction angiography scanner (DSA), an emission computed tomography (ECT), etc.). In some embodiments, the target scanning image may be determined based on a CT imaging device.

In some embodiments, the second obtaining module 330 may obtain a plurality of scanning images of the target object before the radiotherapy or at the target radiation time point. The plurality of scanning images may include a plurality of phase images of the target object corresponding to a plurality of phases. The second obtaining module 330 may determine a plurality of prediction phase images of the target object corresponding to the plurality of phases at the target radiation time point, and determine a matched image that matches the radiation auxiliary image from the plurality of prediction phase images. The matched image may be the prediction phase image most similar to the radiation auxiliary image corresponding to the target radiation time point. For example, the state of the target object in the matched image may be most similar to the state of the target object in the radiation auxiliary image. In some embodiments, a difference between the radiation auxiliary image and the matched image that matches the radiation auxiliary image may be less than a preset value. The second obtaining module 330 may designate a phase image corresponding to the phase of the matched image as the target scanning image. More descriptions of obtaining the target scanning image may be found elsewhere in the present disclosure (e.g., FIG. 7 and descriptions thereof).

In 408, the radiation dose received by the target object at the target radiation time point may be determined based on the target fluence map, the target scanning image, and the data related to radiation source. The operation 408 may be performed by the second determination module 340.

In some embodiments, the second determination module 340 may determine the radiation dose received by the target object at the target radiation time point using the Monte Carlo Method. In some embodiments, the Monte Carlo method may be used to simulate various physical processes of ray particles in the target object (e.g., scattering, attenuation, etc.). In some embodiments, the second determination module 340 may simulate a transport process of the ray particles using the Monte Carlo method. For example, under a parameter condition of devices and/or assemblies used for ray delivery as reflected by the data related to radiation source and a condition of the radioactive source reflected by the target fluence map, after passing through an inner region of the target object reflected by the target scanning image, a final dose distribution may be obtained. Based on the dose distribution, the second determination module 340 may determine the radiation dose received by the target object at the target radiation time point.

In some embodiments, the processing device 130 may further include a third determination module (not shown). The third determination module may obtain the radiation doses received by the target object during radiation at a plurality of target radiation time points and determine a total radiation dose received by the target object during the radiotherapy based on the radiation doses received at the plurality of target radiation time points. Each radiation time point may correspond to a gantry angle. The gantry angle may refer to a rotation angle of the gantry of the radiation device, which may be indicated by the control nodes specified in a radiation treatment plan. The radiation device may deliver ray(s) continuously to the target object at each gantry angle or deliver ray(s) within an angle range between the two gantry angles. The processing device 130 may determine the radiation dose received by the target object under each gantry angle and add these radiation doses to determine the total radiation dose received by the target object during the radiation.

In some embodiments, the processing device 130 may traverse the radiation doses received by the target object at the plurality of target radiation time points corresponding to the plurality of gantry angles in radiation, and determine the total radiation dose received by the target object during the radiation. It may be understood that, in some embodiments, the processing device 130 may calculate the plurality of radiation doses corresponding to the plurality of gantry angles in a fraction of the radiation, and sum the plurality of radiation doses to obtain the total radiation dose received by the target object during the radiation. In some embodiments, the processing device 130 may sequentially calculate the plurality of radiation doses corresponding to each gantry angle in the radiation. In some embodiments, during the process of sequential calculation, the processing device 130 may sum the calculated radiation doses, and finally obtain the total radiation dose. For example, after calculating two radiation doses (e.g., a first radiation dose and a second radiation dose) corresponding to two gantry angles (e.g., a first gantry angle and a second gantry angle), the two radiation doses may be summed, and after calculating a third radiation dose corresponding to a third gantry angle, a sum of the two previously obtained radiation doses may be summed with the newly calculated radiation dose (e.g., the third radiation dose), and so on, until the radiation doses corresponding to all gantry angles are calculated, and the total radiation dose may be obtained.

It should be noted that the above description of the process 400 is merely provided for the purposes of illustration, and not intended to limit the scope of the present disclosure. For those skilled in the art, various modifications and changes may be made to the process 400 under the guidance of the present disclosure. However, those variations and modifications do not depart from the scope of the present disclosure.

Figure 5:
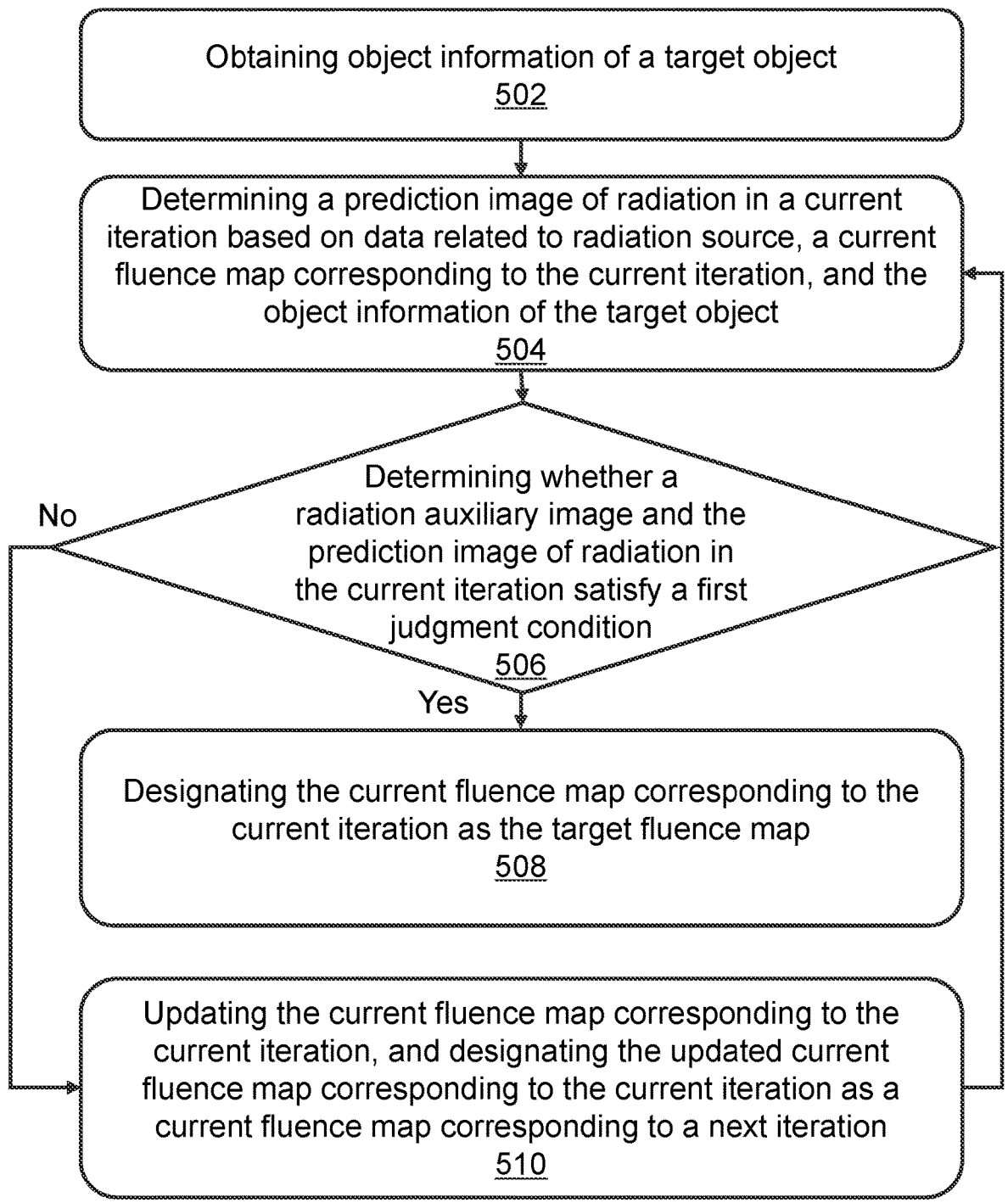
FIG. 5 is a flowchart illustrating an exemplary current iteration of one or more iterations according to some embodiments of the present disclosure.

FIG. 5 is a flowchart illustrating an exemplary current iteration of the one or more iterations according to some embodiments of the present disclosure. In some embodiments, process 500 may be executed by the system 100. For example, the process 500 may be implemented as a set of instructions (e.g., an application) stored in a storage device (e.g., the storage device 150, and/or the memory 220). In some embodiments, the processing device 130 (e.g., the processor 210 of the computing device 200, and/or one or more modules illustrated in FIG. 3) may execute the set of instructions and may accordingly be directed to perform the process 500. The operations of the illustrated process presented below are intended to be illustrative. In some embodiments, the process 500 may be accomplished with one or more additional operations not described and/or without one or more of the operations discussed. Additionally, the order of the operations of process 500 illustrated in FIG. 5 and described below is not intended to be limiting.

In 502, object information of the target object may be obtained.

In some embodiments, the object information of the target object may include scanning image information of the target object. The exemplary scanning image information may include CR image information, DR image information, CT image information, MRI image information, PET image information, or any combination thereof. In some embodiments, the object information may be obtained before the target radiation time point. For example, before the target radiation time point, a CT image obtained by performing CT scanning on the target object may be used as the object information of the target object. In some embodiments, the object information may be pre-stored in the storage device (e.g., the storage device 150). In some embodiments, the first determination module 320 may communicate with the storage device 150 to obtain the object information.

In 504, a prediction image of radiation in a current iteration may be determined based on the data related to radiation source, a current fluence map corresponding to the current iteration, and the object information of the target object.

In some embodiments, the prediction image of radiation may be used to indicate a prediction distribution map formed on the detection assembly (e.g., the imaging assembly 115 of the radiation device 110) after the movement of a plurality of particles of the radiation rays. In some embodiments, the first determination module 320 may determine a prediction image of radiation in the current iteration based on the data related to radiation source, the current fluence map corresponding to the current iteration, and the object information of the target object using the Monte Carlo Method.

For example, the first determination module 320 may simulate each particle in the radiation rays using the Monte Carlo method under the parameter condition of devices and/or assemblies used for ray delivery as reflected by the data related to radiation source and the condition of the radioactive source reflected by the target fluence map, through the transport process under a load free condition (e.g., there is no target object) and through the inner area of the target object reflected by the object information. The particles in each of the two cases may be captured by the detection assembly separately to obtain an image. An image intensity ratio of the two images (e.g., in the case with no target object and the case with the target object) may be referred to as a preset projection ratio. By multiplying the current fluence map corresponding to the current iteration by the preset projection ratio, the prediction image of radiation may be obtained.

It may be understood that the process of determining the target fluence map may be a process of a plurality of iterations. The fluence map corresponding to each iteration may be updated. For example, the current fluence map corresponding to the current iteration may be directly designated as the target fluence map in subsequent operations of the process 500 or may be updated for the next iteration. Therefore, a current fluence map corresponding to an iteration may be an updated fluence map corresponding to a previous iteration. A current fluence map corresponding to an initial iteration of the one or more iterations may be the initial fluence map.

In 506, whether the radiation auxiliary image and the prediction image of radiation in the current iteration satisfy a first judgment condition may be determined.

In some embodiments, the first judgment condition may include the prediction image of radiation in the current iteration being convergent to the radiation auxiliary image. The convergence may mean that a difference between the prediction image of radiation in the current iteration and the radiation auxiliary image is less than a preset threshold. The difference may include a difference between pixel values of corresponding pixels in two images. For example, the difference may be represented by a matrix. For example, a value in the matrix may represent a difference between the pixel values of corresponding two pixels. The difference between the two images being smaller than the preset threshold may mean that a modulus of the matrix representing the difference or an eigenvalue of the matrix is smaller than the preset threshold. The preset threshold may be predetermined or may be adjusted.

In some embodiments, if the radiation auxiliary image and the prediction image of radiation in the current iteration satisfy the first judgment condition (e.g., the prediction image of radiation in the current iteration being convergent to the radiation auxiliary image), the process 500 may proceed to operation 508. If the radiation auxiliary image and the prediction image of radiation in the current iteration do not satisfy the first judgment condition, the process 500 may proceed to operation 510.

In 508, in response to the radiation auxiliary image and the prediction image of radiation in the current iteration satisfying the first judgment condition, the current fluence map corresponding to the current iteration may be designated as the target fluence map.

In some embodiments, if the radiation auxiliary image and the prediction image of radiation in the current iteration satisfy the first judgment condition, the first determination module 320 may designate the current fluence map corresponding to the current iteration as the target fluence map. It may mean that the current fluence map corresponding to the current iteration may reflect the relevant state information of the radioactive source at the target radiation time may be used to determine the subsequence radiation dose.

In 510, in response to the radiation auxiliary image and the prediction image of radiation in the current iteration do not satisfy the first judgment condition, updating the current fluence map corresponding to the current iteration, and designating the updated current fluence map corresponding to the current iteration as a current fluence map corresponding to a next iteration.

In some embodiments, when the radiation auxiliary image and the prediction image of radiation in the current iteration do not satisfy the first judgment condition (i.e., the prediction image of radiation in the current iteration being not convergent to the radiation auxiliary image), the current fluence map corresponding to the current iteration may be updated. In some embodiments, the first determination module 320 may update the current fluence map corresponding to the current iteration.

In some embodiments, the first determination module 320 may determine a first difference between the radiation auxiliary image and the prediction image of radiation in the current iteration. The difference may be a first difference matrix between a first matrix representing the radiation auxiliary image and a second matrix representing the prediction image of radiation in the current iteration. The first difference matrix may be a difference between the first matrix and the second matrix. For example, the first difference matrix may be obtained by subtracting the second matrix from the first matrix or subtracting the first matrix from the second matrix. In some embodiments, the first difference matrix may be a quotient between the first matrix and the second matrix. For example, the first difference matrix may be obtained by multiplying the first matrix by the inverse of the second matrix or multiplying the second matrix by the inverse of the first matrix. In some embodiments, the first determination module 320 may update the current fluence map corresponding to the current iteration based on the first difference. For example, the first determination module 320 may sum the current fluence map corresponding to the current iteration and the first difference matrix. For instance, the first determination module 320 may sum the first difference matrix and a matrix representing the current fluence map corresponding to the current iteration. An image represented by a matrix obtained after the summation may be used as an updated fluence map.

In some embodiments, the first determination module may designate the updated current fluence map corresponding to the current iteration as the current fluence map corresponding to the next iteration, and enter the next iteration. In this way, one or more operations of 504, 506, 508, and 510 may be performed repeatedly. For example, in the next iteration, the operation 504 may be performed again, that is, the updated fluence map may be used as the current fluence map in the operations 504, 506, 508, or 510 corresponding to the next iteration.

It should be noted that the above description of process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 6:
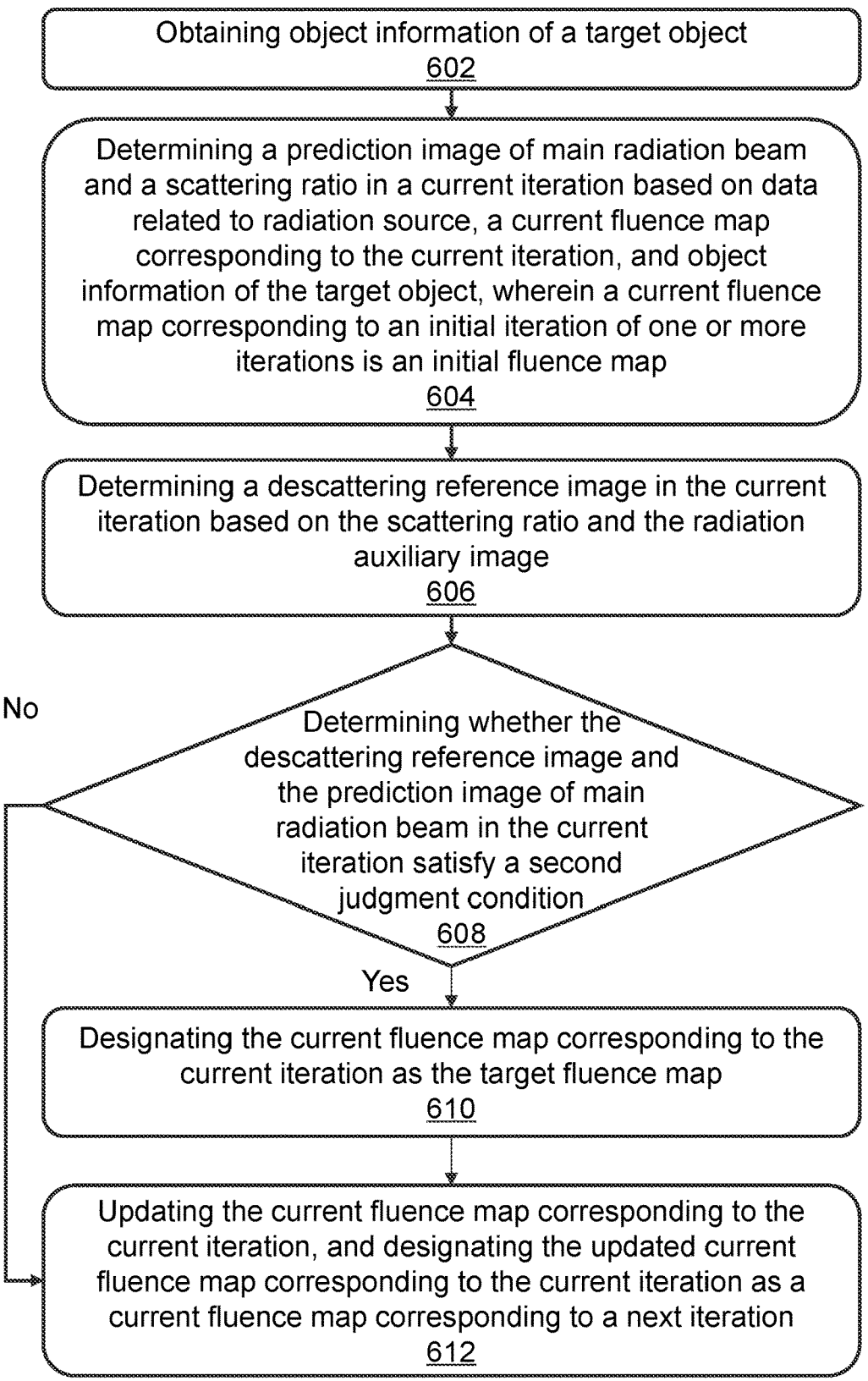
FIG. 6 is a flowchart illustrating another exemplary current iteration of the one or more iterations according to some embodiments of the present disclosure.

FIG. 6 is a flowchart illustrating another exemplary current iteration of the one or more iterations according to some embodiments of the present disclosure. In some embodiments, process 600 may be executed by the system 100. For example, the process 600 may be implemented as a set of instructions (e.g., an application) stored in a storage device (e.g., the storage device 150, and/or the memory 220). In some embodiments, the processing device 130 (e.g., the processor 210 of the computing device 200, and/or one or more modules illustrated in FIG. 3) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In 602, object information of the target object may be obtained.

In some embodiments, the operation 602 may be the same or similar to the operation 502 in process 500. More information about the operation 602 may refer to the operation 502, which may not be repeated here.

In 604, a prediction image of main radiation beam and a scattering ratio in the current iteration may be determined based on the data related to radiation source, a current fluence map corresponding to the current iteration, and object information of the target object. For example, the current fluence map corresponding to a first iteration may be the initial fluence map.

In some embodiments, the prediction image of main radiation beam may be an image formed by chief ray particles after removing scattering particles from the radiation rays. The scattering ratio may be a ratio between the amount of the scattering particles and the amount of the chief ray particles.

In some embodiments, the first determination module 320 may determine a prediction image of main radiation beam and a scattering ratio in the current iteration based on the data related to radiation source, the current fluence map corresponding to the current iteration, and the object information of the target object using the Monte Carlo Method. A current fluence map corresponding to an initial iteration of the one or more iterations is the initial fluence map. For example, the first determination module 320 may simulate each particle in the radiation rays using the Monte Carlo method, under the parameter condition of devices and/or assemblies used for ray delivery as reflected by the data related to radiation source and a condition of the radioactive source reflected by the current fluence map corresponding to the current iteration, and based on a plurality of physical motion processes of an inner region of the target object, and calculate a scattering ratio and an attenuation of particles passing through the target object, to obtain a prediction image of main radiation beam and a scattering image. The first determination module 320 may designate a ratio between the prediction image of main radiation beam and the scattering image as the scattering ratio. For example, the scattering ratio may be represented by $SPR_n(X,Y)=S_n(X,Y)/P_n(X,Y)$, in which n denotes an integer greater than 0, indicating the current iteration, $S_n(X,Y)$ denotes the scattering image in the nth iteration, and $P_n(X,Y)$ denotes the prediction image of main radiation beam in the nth iteration.

Similarly, the process of determining the target fluence map may include a plurality of iterations. The fluence map corresponding to each iteration may be updated. For example, the current fluence map corresponding to the current iteration may be designated as the target fluence map directly in the sequence operation of the process 700 or may be updated and used in the next iteration. Therefore, a current fluence map corresponding to a current iteration may be an updated fluence map in the previous iteration. The current fluence map corresponding to the first iteration may be the initial fluence map.

In 606, a descattering reference image in the current iteration may be determined based on the scattering ratio and the radiation auxiliary image.

In some embodiments, the descattering reference image may be an image determined by the chief ray particles captured by the detection assembly of the radiation device (e.g., the imaging assembly 115 of the radiation device 110). In some embodiments, the first determination module 320 may determine the descattering reference image $P_n^{mea}(X,Y)$ according to the following Equation:

$$P_n^{mea}(X,Y)=(M(X,Y)/[1+SPR_n(X,Y)])$$

wherein n denotes an integer greater than 0, indicating the current iteration, M(X, Y) denotes the radiation auxiliary image, and $SPR_n(X,Y)$ denotes the scattering image in the current nth iteration.

In 608, whether the descattering reference image and the prediction image of main radiation beam in the current iteration satisfy a second judgment condition may be determined.

In some embodiments, the second judgment condition may include the prediction image of main radiation beam in the current iteration being convergent to the descattering reference image in the current iteration. The convergence may mean that a difference between the prediction image of main radiation beam in the current iteration and the descattering reference image in the current iteration is less than a preset threshold. The difference may be related to a difference between pixel values of corresponding pixels in the two images. For example, the difference may be represented by a matrix. For example, a value in the matrix may represent a difference between the pixel values of corresponding two pixels of the two images. The difference being smaller than the preset threshold may mean that the modulus of the matrix representing the difference or an eigenvalue of the matrix is smaller than the preset threshold. The preset threshold value may be predetermined or may be adjusted.

In some embodiments, if the descattering reference image and the prediction image of main radiation beam in the current iteration satisfy a second judgment condition, the process 600 may proceed to operation 610. If the descattering reference image and the prediction image of main radiation beam in the current iteration do not satisfy the second judgment condition, the process 600 may proceed to operation 612.

In 610, in response to the descattering reference image and the prediction image of main radiation beam in the current iteration satisfying the second judgment condition, the current fluence map corresponding to the current iteration may be designated as the target fluence map.

In some embodiments, if the descattering reference image and the prediction image of main radiation beam in the current iteration satisfy the second judgment condition, the first determination module may designate the current fluence map corresponding to the current iteration as the target fluence map. It may mean that the current fluence map corresponding to the current iteration can reflect the state information of the radioactive source at the target radiation time point and may be used to determine the subsequence radiation dose.

In 612, in response to the descattering reference image and the prediction image of main radiation beam in the current iteration not satisfying the second judgment condition, the current fluence map corresponding to the current iteration may be updated, and the updated current fluence map corresponding to the current iteration may be designated as a current fluence map corresponding to a next iteration.

In some embodiments, if the descattering reference image and the prediction image of main radiation beam in the current iteration do not satisfy the second judgment condition, the current fluence map corresponding to the current iteration may be updated. In some embodiments, the first determination module 320 may update the current fluence map corresponding to the current iteration, and designate the updated current fluence map corresponding to the current iteration as a current fluence map corresponding to a next iteration.

In some embodiments, the first determination module 320 may determine a second difference between the descattering reference image and the prediction image of main radiation beam in the current iteration. The second difference may be a second difference matrix between a third matrix representing the descattering reference image in the current iteration and a fourth matrix representing the prediction image of main radiation beam in the current iteration. The second difference matrix may be a difference between the third matrix and the fourth matrix. For example, the second difference matrix may be obtained by subtracting the fourth matrix from the third matrix. In some embodiments, the second difference matrix may be a quotient between the third matrix and the fourth matrix. For example, the second difference matrix may be obtained by multiplying the third matrix by the inverse of the fourth matrix. In some embodiments, the first determination module 320 may update the current fluence map corresponding to the current iteration based on the second difference. For example, the first determination module 320 may sum the current fluence map corresponding to the current iteration and the second difference matrix. For instance, the first determination module 320 may sum the second difference matrix and the matrix representing the current fluence map corresponding to the current iteration, and designate an image represented by a matrix obtained after the summation as the updated fluence map.

It should be noted that the above description of process 600 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Based on the description of the foregoing flowchart, the radiation dose at the target radiation time point may be determined by using the information of the target scanning image corresponding to the target radiation time point. The target scanning image may reflect the state of the target object at the target radiation time point. At this time, the more accurate the state of the target object reflected by the target scanning image, the more accurate the result of the determined radiation dose.

Figure 7:
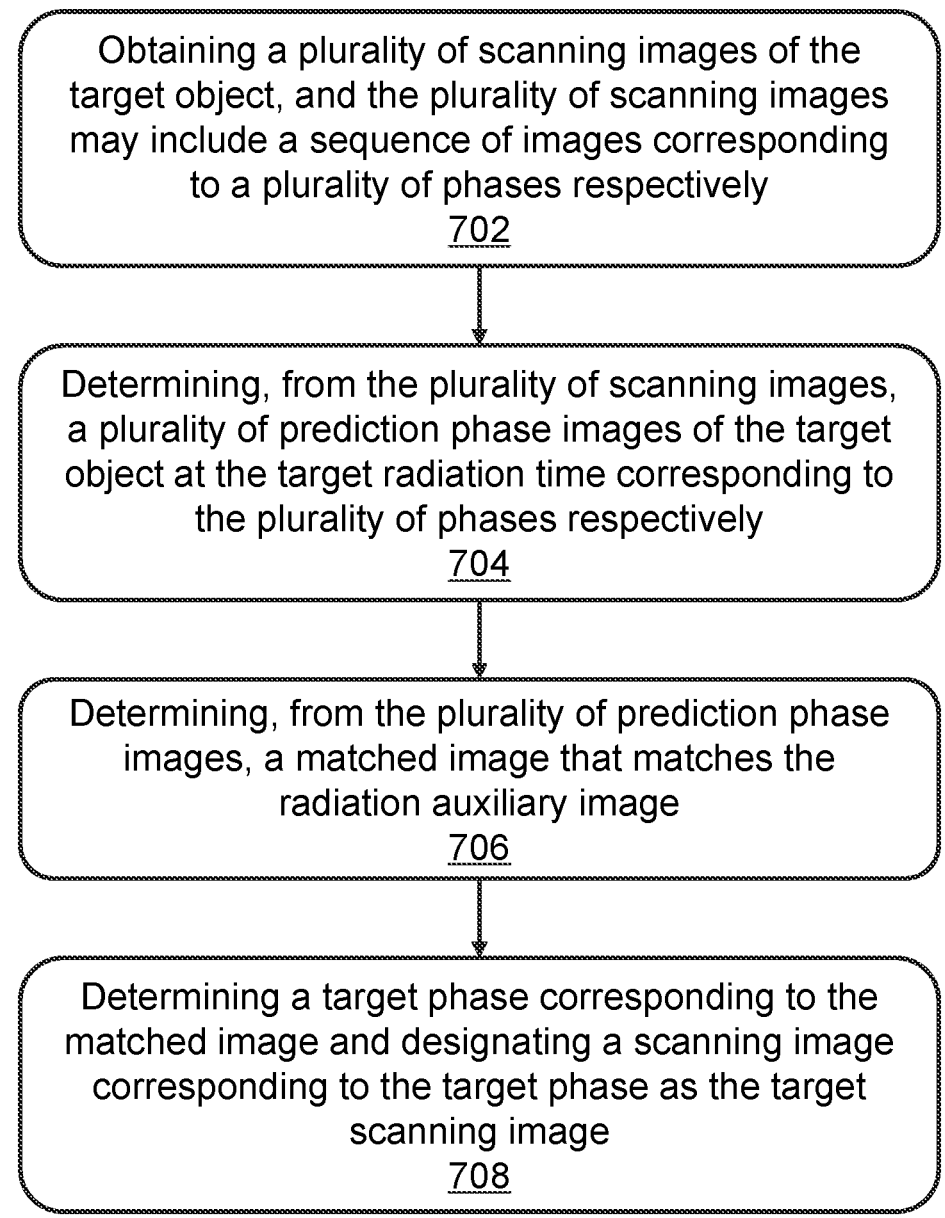
FIG. 7 is a flowchart illustrating an exemplary process for obtaining a target scanning image of a target object according to some embodiments of the present disclosure.

FIG. 7 is a flowchart illustrating an exemplary process for obtaining a target scanning image of a target object according to some embodiments of the present disclosure. In some embodiments, process 700 may be executed by the system 100. For example, the process 700 may be implemented as a set of instructions (e.g., an application) stored in a storage device (e.g., the storage device 150, and/or the memory 220). In some embodiments, the processing device 130 (e.g., the processor 210 of the computing device 200, and/or one or more modules illustrated in FIG. 3) may execute the set of instructions and may accordingly be directed to perform the process 700. The operations of the illustrated process presented below are intended to be illustrative. In some embodiments, the process 700 may be accomplished with one or more additional operations not described and/or without one or more of the operations discussed. Additionally, the order of the operations of process 700 illustrated in FIG. 7 and described below is not intended to be limiting.

In 702, a plurality of scanning images of the target object may be obtained, and the plurality of scanning images may include a sequence of images corresponding to a plurality of phases respectively.

In some embodiments, the plurality of scanning images may include a plurality of scanning images reflecting different motion states of the target object in one or more autonomous motion cycles. For example, the scanning images may include scanning images of the chest of a lung cancer patient in various states such as exhalation and inhalation in one or more breathing cycles. In the present disclosure, the state of the target object may also be referred to as a phase. The plurality of scanning images may correspond to different phases respectively. The breathing cycles may be divided into the plurality of phases. The scanning images may be 4D images, which may include a sequence of images corresponding to different time points, representing the scanning images corresponding to different phases in breathing cycles.

In some embodiments, the sequence of images corresponding to the plurality of phases may be captured within a preset time before a current fraction of the radiation to which the target radiation time point belongs.

In some embodiments, the plurality of scanning images may be determined by pre-scanning before the target radiation time point. For example, the target object may be scanned and imaged before the target radiation time point, to obtain the plurality of scanning images. As another example, the target object may be scanned and imaged in a preset time period (e.g., one week) before the target radiation time point, to obtain the plurality of scanning images. As a further example, the target object may be scanned and imaged periodically (e.g., once a week), to obtain the plurality of scanning images. In some embodiments, the plurality of scanning images may be reconstructed based on scanning data acquired in a most recent cycle before the fraction of the radiation to which the target radiation time point belongs. For example, the plurality of scanning images may be obtained before the beginning of a current radiation fraction. As another example, the plurality of scanning images may be obtained online. The online obtaining may refer to starting the radiation fraction after scanning the target object to obtain the images, and the target object does not need to leave the bed. It may be understood that the closer the scanning time is to the radiation time, the higher the accuracy of the obtained scanning image may be. Therefore, the plurality of online obtained scanning images may be more accurate. Further, the plurality of scanning images of the target object may be obtained online, and the images obtained at the beginning, during, or after the radiation may be highly matched with the state of the patient during the radiation, and thus, the radiation dose reconstructed based on the scanning images may be more accurate.

In some embodiments, the plurality of scanning images may include a plurality of four-dimensional computed tomography (4D-CT) images obtained by a 4D-CT imaging device. Since the 4D-CT provides a time dimension, the state of the target object at each time point may be reflected better. Compared with a time volume image obtained by a traditional CT, the 4D-CT image may reflect an actual state of the target object, and thus, the influence due to the motion of the target object may be eliminated in a greater extent. At the same time, since the acquisition of the plurality of scanning images may be performed before the radiation, the influence of posture changes (e.g., a patient's body shape change) and positioning of the target object may be eliminated.

In some embodiments, a target scanning image may be determined from the plurality of scanning images based on the radiation auxiliary image. In some embodiments, the target scanning image may be determined from the plurality of scanning images using one or more algorithms (e.g., an image processing algorithm) based on the radiation auxiliary image, which may not be limited in the present disclosure.

In 704, a plurality of prediction phase images of the target object at the target radiation time point corresponding to the plurality of phases may be determined from the plurality of scanning images.

In some embodiments, a prediction phase image may refer to a prediction image reflecting the state of the target object at the target radiation time point.

In some embodiments, in order to determine the plurality of prediction phase images corresponding to the plurality of phases, the second obtaining module 330 may obtain treatment planning information. The treatment planning information may be determined before the radiotherapy. For example, the treatment planning information of the target object may be determined based on a planning CT image. The treatment planning information may include state information of one or more treatment assemblies at the target radiation time point. For example, the treatment planning information may specify a plurality of control nodes, and each control node may correspond to a time point. The treatment planning information may include the state of each assembly of the radiation device at each control node, such as a rotation angle, a gantry speed, a moving position and a moving speed of the leaves and/or a tungsten gate of the collimator (e.g., a multi-leaf collimator), an intensity/energy of the rays emitted by the accelerator, a position of the treatment bed, etc. The second obtaining module 330 may determine planning delivery information at the target radiation time point based on the treatment planning information. The time corresponding to a control node may be the radiation time. At this time, the radiation device may start the ray delivery. Therefore, the second obtaining module 330 may determine planning delivery information at the target radiation time point based on the treatment planning information. The planning delivery information may include radiation beam angles and a segment parameter corresponding to each of the radiation beam angles. In some embodiments, the planning delivery information may further include a radiation beam intensity, a radiation beam conformal shape, a radiation dose, etc.

In some embodiments, for each phase of the plurality of phases, the second obtaining module 330 may obtain information relating to the phase. The information relating to the phase may include state information or stage information of the target object under the phase. For example, the information relating to the phase may include a stage of physiological movement (e.g., systolic phase of cardiac movement, diastolic phase of cardiac movement, etc.) of the target object (e.g., a patient, organ, or tissue of a patient), a posture of the target object (such as lying down, lying on the side, etc.), and/or a body shape of the target object, etc. In some embodiments, the second obtaining module may determine the prediction phase image corresponding to the phase based on the planning delivery information and the scanning image corresponding to the phase. For example, the second obtaining module 330 may simulate an initial state of each particle in the radiation rays when the imaging device delivers the radiation rays and a physical movement process of the particle before and after the particle passes through the target object (e.g., scattering, attenuation, etc.) based on the planning delivery information to obtain a state of the each particle when it is finally captured by the detection assembly of the radiation device (e.g., an energy, a speed, a motion direction, etc.) and a distribution result of all particles. The second obtaining module 330 may obtain the prediction phase image based on the above data (e.g., the state of the each particle, the distribution result of all particles, etc.).

In 706, a matched image that matches the radiation auxiliary image may be determined from the plurality of prediction phase images.

In some embodiments, the matched image may refer to a prediction phase image most similar to the radiation auxiliary image corresponding to the target radiation time point. For example, the state of the target object displayed in the matched image may be the most similar to the state of the target object displayed in the radiation auxiliary image. In some embodiments, the second obtaining module 330 may determine the matched image that matches the radiation auxiliary image using a feature matching algorithm. For example, the second obtaining module 330 may compare a feature distribution (e.g., a grayscale distribution feature) of the plurality of prediction phase images with a grayscale distribution feature of the radiation auxiliary image and choose the prediction phase image whose feature distribution is most similar to the grayscale distribution feature of the radiation auxiliary image as the matched image.

In some embodiments, the second obtaining module may determine first position information including a target tissue in the radiation auxiliary image, and second position information including the target tissue in each prediction phase image of the plurality of prediction phase images. The target tissue may refer to an identifiable tissue in the target object. For example, if the target object is the chest of lung cancer patient, the target object may be a tumor area or a lung organ. The first position information may be used to represent position of the target tissue in the radiation auxiliary image, which may be represented by a corresponding coordinate range. For example, the first position information may be represented by the coordinate range of pixels that belong to the target tissue in the radiation auxiliary image in the image coordinate system. Similar to the first position information, the second position information may be used to represent position of the target tissue in the prediction phase image, which may be represented by a corresponding coordinate range. For example, the second position information may be represented by the coordinate range of the pixels that belong to the target tissue in the prediction phase image in the image coordinate system.

In some embodiments, the second obtaining module 330 may determine the matched image that matches the radiation auxiliary image based on the first position information and the second position information. For example, the second obtaining module 330 may compare the first position information with the second position information corresponding to each prediction phase image. If the first position information matches the second position information corresponding to the prediction phase image (e.g., a difference between the coordinate ranges of the first position information and the second position information may be smaller than a preset range), the second obtaining module 330 may designate the prediction phase image as the matched image.

In some embodiments, the second obtaining module 330 may determine a third difference of each prediction phase image in the plurality of prediction phase images and the radiation auxiliary image. The third difference may refer to a difference between a matrix representing the radiation auxiliary image and a matrix representing the prediction phase image. For example, the third difference may be a matrix subtraction result obtained by subtracting the matrix representing the prediction phase image from the matrix representing the radiation auxiliary image. As another example, the third difference may be a matrix multiplication result obtained by multiplying the matrix representing the radiation auxiliary image by an inverse matrix of the matrix representing the prediction phase image. The second obtaining module 330 may determine a minimum value in the plurality of the third differences, and designate the prediction phase image corresponding to the minimum value as the matched image. For example, the second obtaining module 330 may determine a modulus or eigenvalue of the matrix subtraction result or matrix multiplication result representing a third difference, and designate the prediction phase image corresponding to the minimum modulus or eigenvalue as the matched image.

In 708, a target phase corresponding to the matched image may be determined and a scanning image corresponding to the target phase may be designated as the target scanning image.

In some embodiments, since the matched image is one of the plurality of the prediction phase images corresponding to the plurality of phases, after determining the matched image, the second obtaining module 330 may directly designate the phase corresponding to the matched image as the target phase. Then, the second obtaining module 330 may determine the scanning image corresponding to the target phase as the target scanning image.

It should be noted that the above description of process 700 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 8 is a flowchart illustrating an exemplary process for determining a fluence map according to some embodiments of the present disclosure. In some embodiments, process 800 may be executed by the system 100. For example, the process 800 may be implemented as a set of instructions (e.g., an application) stored in a storage device (e.g., the storage device 150, and/or the memory 220). In some embodiments, the processing device 130 (e.g., the processor 210 of the computing device 200, and/or one or more modules illustrated in FIG. 3) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting.

In 802, a radiation auxiliary image of a target object at a target radiation time point and an initial fluence map corresponding to the target radiation time point may be obtained.

In 804, a target fluence map corresponding to the target radiation time point may be determined by one or more iterations at least based on the radiation auxiliary image, the initial fluence map, and data related to radiation source.

In some embodiments, the target fluence map may be used to reconstruct the radiation dose (as shown in FIG. 4), and/or may be used for other purposes, such as feature extraction, model training, etc., which may not be limited in the present disclosure.

More descriptions about the process 800 may be found in FIG. 4 and the related descriptions, such as the operation 402 and the operation 404.

FIG. 9 is a flowchart illustrating an exemplary process for determining a radiation dose according to some embodiments of the present disclosure. In some embodiments, process 900 may be executed by the system 100. For example, the process 900 may be implemented as a set of instructions (e.g., an application) stored in a storage device (e.g., the storage device 150, and/or the memory 220). In some embodiments, the processing device 130 (e.g., the processor 210 of the computing device 200, and/or one or more modules illustrated in FIG. 3) may execute the set of instructions and may accordingly be directed to perform the process 900. The operations of the illustrated process presented below are intended to be illustrative. In some embodiments, the process 900 may be accomplished with one or more additional operations not described and/or without one or more of the operations discussed. Additionally, the order of the operations of process 900 illustrated in FIG. 9 and described below is not intended to be limiting.

In 902, a radiation auxiliary image of a target object at a target radiation time point may be obtained.

More descriptions about the operation 902 may be found in the operation 402 of FIG. 4 and the related descriptions in the present disclosure.

In 904, a plurality of scanning images of the target object may be obtained, the plurality of scanning images may include a sequence of images corresponding to a plurality of phases respectively.

In some embodiments, the plurality of scanning images may include 4D-CT images obtained using an imaging device or online 4D-CT images.

More descriptions about the operation 904 may be found in the operation 702 of FIG. 7 and the related descriptions in the present disclosure.

In 906, a target scanning image may be determined from the plurality of scanning images based on the radiation auxiliary image.

In some embodiments, the processing device may determine a plurality of prediction phase images of the target object at the target radiation time point corresponding to the plurality of phases respectively from the plurality of scanning images, determine a matched image that matches the radiation auxiliary image from the plurality of prediction phase images, determine a target phase corresponding to the matched image, and/or designate a scanning image corresponding to the target phase as the target scanning image.

More descriptions about determining the target scanning image may be found in the operations 704-708 of FIG. 7 and the related descriptions in the present disclosure.

In 908, the radiation dose received by the target object at the target radiation time point may be determined based on the target scanning image and the radiation auxiliary image.

In some embodiments, the processing device may obtain the target fluence map based on the radiation auxiliary image, and determine the radiation dose received by the target object at the target radiation time point based on the target fluence map and the target scanning image.

For example, the processing device may determine the target fluence map corresponding to the target radiation time point by the one or more iterations based on the radiation auxiliary image, the initial fluence map, and the data related to radiation source. More descriptions about determining the target fluence map may be found in the operation 404 of FIG. 4 and the related descriptions in the present disclosure.

In some embodiments, the processing device may determine the radiation dose received by the target object at the target radiation time point, based on the target fluence map, the target scanning image, and the data related to radiation source using the Monte Carlo Method. More descriptions about determining the radiation dose may be found in the operation 408 of FIG. 4 and the related descriptions in the present disclosure In some embodiments, the processing device may reconstruct the dose through various dose calculation engines to determine the radiation dose received by the target object at the target radiation time point based on the target fluence map and the target scanning image. In some embodiments, the processing device may reconstruct the dose using a convolution superposition algorithm or any other algorithm to determine the radiation dose received by the target object at the target radiation time point based on the target fluence map and the target scanning image.

According to some embodiments of the present disclosure, (1) by combining data related to radiation source with a forward iterative process, the computational complexity is reduced and the computational accuracy is improved; (2) by using 4D-CT image(s) in the dose reconstruction, the motion influence on dose reconstruction can be eliminated, and the influence of posture changes and positioning of the target object (e.g., the patient) can be eliminated. It should be noted that different embodiments may provide different beneficial effects. In different embodiments, the possible beneficial effects may be any one or a combination of the above, or any other possible beneficial effect.

The basic concepts have been described. Obviously, for those skilled in the art, the detailed disclosure may be only an example and may not constitute a limitation to the present disclosure. Although not explicitly stated here, those skilled in the art may make various modifications, improvements, and amendments to the present disclosure. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of the specification are not necessarily all referring to the same embodiment. In addition, some features, structures, or features in the present disclosure of one or more embodiments may be appropriately combined.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, all aspects of the present disclosure may be performed entirely by hardware, may be performed entirely by software (including firmware, resident software, microcode, etc.), or may be performed by a combination of hardware and software. The above hardware or software may be referred to as "data block", "module", "engine", "unit", "component". or "system". In addition, aspects of the present disclosure may appear as a computer product located in one or more computer-readable media, the product including computer-readable program code.

A computer storage medium may include a propagation data signal containing a computer program encoding, such as on a baseband or as part of a carrier. The propagation signal may have a variety of expressions, including an electromagnetic form, an optical form, or a suitable combination form. The computer storage medium may be any computer-readable medium other than the computer-readable storage medium, which may be used to perform system, devices, or devices to implement communication, propagating, or devices by connecting to an instruction. The program code located on the computer storage medium may be propagated through any suitable medium, including radio, cable, fiber optic cable, RF, or similar media, or any combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter case, the remote computer may be connected to the user's computer through any network, such as a local area network (LAN) or a wide area network (WAN), or connected to an external computer (e.g., via the Internet), or in a cloud computing environment, or as a service use such as software as a service (SaaS).

Moreover, unless otherwise specified in the claims, the sequence of the processing elements and sequences of the present application, the use of digital letters, or other names are not used to define the order of the application flow and methods. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various assemblies described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure and aiding in the understanding of one or more of the various embodiments. However, this disclosure may not mean that the present disclosure object requires more features than the features mentioned in the claims. In fact, the features of the embodiments are less than all of the features of the individual embodiments disclosed above.

In some embodiments, the numbers expressing quantities, properties, and so forth, used to describe and claim certain embodiments of the application are to be understood as being modified in some instances by the term "about," "approximate," or "substantially." Unless otherwise stated, "about," "approximate," or "substantially" may indicate a ±20% variation of the value it describes. Accordingly, in some embodiments, the numerical parameters set forth in the description and attached claims are approximations that may vary depending upon the desired properties sought to be obtained by a particular embodiment. In some embodiments, the numerical parameters should be construed in light of the number of reported significant digits and by applying ordinary rounding techniques. Although the numerical domains and parameters used in the present application are used to confirm the range of ranges, the settings of this type are as accurate in the feasible range in the feasible range in the specific embodiments.

Each patent, patent application, patent application publication, and other materials cited herein, such as articles, books, instructions, publications, documents, etc., are hereby incorporated by reference in the entirety. In addition to the application history documents that are inconsistent or conflicting with the contents of the present disclosure, the documents that may limit the widest range of the claim of the present disclosure (currently or later attached to this application) are excluded from the present disclosure. It should be noted that if the description, definition, and/or terms used in the appended application of the present disclosure is inconsistent or conflicting with the content described in the present disclosure, the use of the description, definition and/or terms of the present disclosure shall prevail.

At last, it should be understood that the embodiments described in the disclosure are used only to illustrate the principles of the embodiments of this application. Other modifications may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A system for determining a radiation dose in a radiotherapy, comprising:
    at least one storage device storing a set of instructions; and
    at least one processor in communication with the storage device, wherein when executing the set of instructions, the at least one processor is configured to cause the system to perform operations including:
    obtaining data related to radiation source, a radiation auxiliary image of a target object at a target radiation time point, and an initial fluence map corresponding to the target radiation time point;
    determining a target fluence map corresponding to the target radiation time point by one or more iterations based on the radiation auxiliary image, the initial fluence map, and the data related to radiation source;
    obtaining a target scanning image of the target object; and
    determining the radiation dose received by the target object at the target radiation time point, based on the target fluence map, the target scanning image, and the data related to radiation source.

2. The system of claim 1, wherein a current iteration of the one or more iterations includes:
    determining a prediction image of radiation in the current iteration based on the data related to radiation source, a current fluence map corresponding to the current iteration, and object information of the target object;
    determining whether the radiation auxiliary image and the prediction image of radiation in the current iteration satisfy a first judgment condition;
    in response to the radiation auxiliary image and the prediction image of radiation in the current iteration satisfying the first judgment condition, designating the current fluence map corresponding to the current iteration as the target fluence map; and in response to the radiation auxiliary image and the prediction image of radiation in the current iteration not satisfying the first judgment condition, updating the current fluence map corresponding to the current iteration, and designating the updated current fluence map corresponding to the current iteration as a current fluence map corresponding to a next iteration.

3. The system of claim 2, wherein the first judgment condition includes:
the prediction image of radiation in the current iteration being convergent to the radiation auxiliary image.

4. The system of claim 2, wherein the updating the current fluence map corresponding to the current iteration includes:
determining a first difference between the radiation auxiliary image and the prediction image of radiation in the current iteration; and
updating the current fluence map corresponding to the current iteration based on the first difference.

5. The system of claim 1, wherein a current iteration of the one or more iterations includes:
determining a prediction image of main radiation beam and a scattering ratio in the current iteration based on the data related to radiation source, a current fluence map corresponding to the current iteration, and object information of the target object;
determining a descattering reference image in the current iteration based on the scattering ratio and the radiation auxiliary image;
determining whether the descattering reference image and the prediction image of main radiation beam in the current iteration satisfy a second judgment condition;
in response to the descattering reference image and the prediction image of main radiation beam in the current iteration satisfying the second judgment condition, designating the current fluence map corresponding to the current iteration as the target fluence map; and
in response to the descattering reference image and the prediction image of main radiation beam in the current iteration not satisfying the second judgment condition, updating the current fluence map corresponding to the current iteration, and designating the updated current fluence map corresponding to the current iteration as a current fluence map corresponding to a next iteration.

6. The system of claim 5, wherein the updating the current fluence map corresponding to the current iteration includes:
determining a second difference between the descattering reference image and the prediction image of main radiation beam in the current iteration; and
updating the current fluence map corresponding to the current iteration based on the second difference.

7. The system of claim 5, wherein the second judgment condition includes:
the prediction image of main radiation beam in the current iteration being convergent to the descattering reference image in the current iteration.

8. The system of claim 1, wherein the obtaining a target scanning image of the target object includes:
obtaining a plurality of scanning images of the target object, the plurality of scanning images including a sequence of images corresponding to a plurality of phases respectively; and
determining the target scanning image from the plurality of scanning images based on the radiation auxiliary image.

9. The system of claim 8, wherein the plurality of scanning images include one or more four-dimensional computed tomography (4D-CT) images obtained based on an imaging device or one or more online 4D-CT images.

10. The system of claim 8, wherein the determining the target scanning image from the plurality of scanning images based on the radiation auxiliary image includes:
determining, from the plurality of scanning images, a plurality of prediction phase images of the target object at the target radiation time point corresponding to the plurality of phases respectively;
determining, from the plurality of prediction phase images, a matched image that matches the radiation auxiliary image;
determining a target phase corresponding to the matched image; and
designating a scanning image corresponding to the target phase as the target scanning image.

11. The system of claim 10, wherein the determining a plurality of prediction phase images corresponding to the plurality of phases respectively includes:
obtaining treatment planning information;
determining planning delivery information at the target radiation time point based on the treatment planning information, wherein the planning delivery information includes one or more radiation beam angles and a segment parameter corresponding to each of the one or more radiation beam angles; and
for each phase of the plurality of phases, determining a prediction phase image corresponding to the phase based on the planning delivery information and a scanning image corresponding to the phase.

12. The system of claim 1, wherein the at least one processor is further configured to cause the system to perform operations including:
determining a total radiation dose radiation received by the target object in the radiation by traversing a plurality of radiation doses received by the target object at a plurality of radiation time points corresponding to a plurality of radiation beam angles in the radiotherapy.

13. The system of claim 1, wherein the radiation auxiliary image includes an electronic portal imaging device (EPID) image.

14. The system of claim 1, wherein the at least one processor is further configured to cause the system to perform operations including:
calibrating the radiation auxiliary image.

15. A system for determining a fluence map, comprising:
at least one storage device storing a set of instructions; and
at least one processor in communication with the storage device, wherein when executing the set of instructions, the at least one processor is configured to cause the system to perform operations including:
obtaining a radiation auxiliary image of a target object at a target radiation time point and an initial fluence map corresponding to the target radiation time point; and
determining a target fluence map corresponding to the target radiation time point by one or more iterations at least based on the radiation auxiliary image, the initial fluence map, and data related to radiation source.

16. A system for determining a radiation dose, comprising:
at least one storage device storing a set of instructions; and
at least one processor in communication with the storage device, wherein when executing the set of instructions, the at least one processor is configured to cause the system to perform operations including:

obtaining a radiation auxiliary image of a target object at a target radiation time point;

obtaining a plurality of scanning images of the target object, the plurality of scanning images including a sequence of images corresponding to a plurality of phases respectively;

determining a target scanning image from the plurality of scanning images based on the radiation auxiliary image; and determining the radiation dose received by the target object at the target radiation time point based on the target scanning image and the radiation auxiliary image.

17. The system of claim 16, wherein the plurality of scanning images include one or more four-dimensional computed tomography (4D-CT) images obtained based on an imaging device or one or more online 4D-CT images.

18. The system of claim 16, wherein the determining a target scanning image from the plurality of scanning images based on the radiation auxiliary image includes:

determining, from the plurality of scanning images, a plurality of prediction phase images of the target object at the target radiation time point corresponding to the plurality of phases respectively;

determining, from the plurality of prediction phase images, a matched image that matches the radiation auxiliary image; and determining a target phase corresponding to the matched image; and designating a scanning image corresponding to the target phase as the target scanning image.

19. The system of claim 18, wherein the determining a plurality of prediction phase images corresponding to the plurality of phases respectively includes:

obtaining treatment planning information;

determining planning delivery information at the target radiation time point based on the treatment planning information, wherein the planning delivery information includes one or more radiation beam angles and a segment parameter corresponding to each of the one or more radiation beam angles; and for each phase of the plurality of phases, determining a prediction phase image corresponding to the phase based on the planning delivery information and a scanning image corresponding to the phase.

20. The system of claim 16, wherein the sequence of images corresponding to the plurality of phases are acquired within a preset time period before a current fractionation of radiation corresponding to the target radiation time point.

* * * * *

UNITED STATES PATENT AND TRADEMARK OFFICE
CERTIFICATE OF CORRECTION

| | | |
|---|---|---|
| PATENT NO. | : 12,121,753 B2 | Page 1 of 1 |
| APPLICATION NO. | : 17/823500 | |
| DATED | : October 22, 2024 | |
| INVENTOR(S) | : Yanfang Liu | |

It is certified that error appears in the above-identified patent and that said Letters Patent is hereby corrected as shown below:

On the Title Page

Foreign Application Priority Data (item (30)), should be added after item (63) and before item (51):
-- The Foreign Application Priority Data
Aug. 30, 2021 (CN) ................ 202111006830.1 --

Signed and Sealed this
Twenty-sixth Day of August, 2025

Coke Morgan Stewart
*Acting Director of the United States Patent and Trademark Office*